United States Patent
Huang (10) Patent No.: US 9,554,705 B2
(45) Date of Patent: Jan. 31, 2017

(54) SYSTEM AND DEVICE FOR MEDICAL MONITORING

(71) Applicant: International Mobile IOT Corp, Taipei (TW)

(72) Inventor: Jung-Tang Huang, Taipei (TW)

(73) Assignee: International Mobile IOT Corp, Taipei (TW)

( * ) Notice: Subject to any disclaimer, the term of this patent is extended or adjusted under 35 U.S.C. 154(b) by 78 days.

(21) Appl. No.: 14/549,564

(22) Filed: Nov. 21, 2014

(65) Prior Publication Data

US 2015/0137997 A1 May 21, 2015

(30) Foreign Application Priority Data

Nov. 21, 2013 (TW) .............................. 102142505 A (51) Int. Cl.
*G08B 1/08* (2006.01)
*A61B 5/00* (2006.01)
*A61B 5/11* (2006.01)
*G06F 19/00* (2011.01)

(52) U.S. Cl.
CPC ............ *A61B 5/0015* (2013.01); *A61B 5/1112* (2013.01); *G06F 19/3418* (2013.01); *A61B 5/6802* (2013.01)

(58) Field of Classification Search
CPC combination set(s) only.
See application file for complete search history.

(56) References Cited

U.S. PATENT DOCUMENTS

| 5,532,709 | A | * | 7/1996 | Talty | H01Q 19/30 343/713 |
| 7,414,534 | B1 | * | 8/2008 | Kroll | A61B 5/0031 128/903 |
| 2003/0001742 | A1 | * | 1/2003 | Eshelman | A61B 5/0002 340/573.1 |
| 2005/0075907 | A1 | * | 4/2005 | Rao | A61B 5/0002 705/2 |

(Continued)

FOREIGN PATENT DOCUMENTS

| CN | 103186712 A | 7/2013 |
| TW | M460478 U | 8/2013 |
| TW | 201347591 A | 11/2013 |

*Primary Examiner* — Brian Zimmerman
*Assistant Examiner* — Cal Eustaquio
(74) *Attorney, Agent, or Firm* — Zhigang Ma (57) ABSTRACT

The present disclosure provides a medical monitoring system which comprises a landmark with a wireless module configured to broadcast a location information, a server connected to the landmark, a wearable device comprising a wearable-end wireless module and a user tag, a monitoring device comprising a monitor-end wireless module and a tag reader, and wherein the tag reader reads a user information from the user tag. The wearable device uses the wearable-end wireless module to receive the location information from the landmark, and determines a first current location based on the location information, and uses the wearable-end wireless module to send the first current location and the user information to the server via the landmark. The monitoring device uses the monitor-end wireless module and the user information as reference to obtain the first current location from the server via the landmark.

27 Claims, 7 Drawing Sheets

(56) References Cited

U.S. PATENT DOCUMENTS

| | | | |
|---|---|---|---|
| 2005/0114154 A1* | 5/2005 | Wolkowicz | G06Q 30/02 340/539.12 |
| 2005/0203349 A1* | 9/2005 | Nanikashvili | A61B 5/0002 600/300 |
| 2007/0008112 A1* | 1/2007 | Covannon | A61J 3/007 340/539.12 |
| 2009/0177769 A1* | 7/2009 | Roberts | G06F 19/327 709/224 |
| 2011/0196201 A1* | 8/2011 | Sato | A61B 1/00009 600/109 |
| 2014/0145822 A1* | 5/2014 | Shoenfeld | G07C 9/00111 340/5.61 |
| 2014/0258403 A1* | 9/2014 | Elmore | H04L 65/403 709/204 |
| 2014/0288945 A1* | 9/2014 | Boerner | G06Q 30/016 705/2 |

* cited by examiner

SYSTEM AND DEVICE FOR MEDICAL MONITORING

FIELD OF THE INVENTION

The present invention relates generally to a device and a system for monitoring, more specifically a medical monitoring system with a wearable device and a monitoring device providing monitoring of location and physiological parameter of the wearable device user.

BACKGROUND OF THE INVENTION

Traditionally, the monitoring around a medical environment only provides RFID tag on patients, and a doctor or nurse may be responsible for several patients, and the RFID tag may only provide the basic information about a patient, wherein the physiological parameter may only be determined by the doctor or nurse with medical equipment when they are around the patient, and thus the physiological parameter of patients is not monitored at a real-time basis.

Furthermore, the physiological parameter of the patients may only be determined with doctor or nurse approaching the patients face to face in proximity, so a patient with emergent health condition may not be noticed by the doctor or nurse straight away if the doctor or nurse is not around. Therefore, knowing the physiological parameter that indicates the patients' health condition and the location of the patients is important to provide first aid in time.

According to the above, a system for medical monitoring is needed to monitor the patients' physiological parameter and location to improve medical service and reduce the time wasted between an emergency event and the first aid.

BRIEF SUMMARY OF THE INVENTION

In view of the foregoing subject, a general objective of the present invention is to provide a device or a system including the device for monitoring. More specifically, a more specific objective of the present invention is to provide a system for medical monitoring.

The invention generally provides a medical monitoring system which may comprise at least one landmark with a wireless module configured to broadcast a location information, a server connected to the at least one landmark, a wearable device comprising a wearable-end wireless module and a user tag, a monitoring device comprising a monitor-end wireless module and a tag reader, and wherein the tag reader is configured to read a user information from the user tag. The wearable device is configured to use the wearable-end wireless module to receive the location information from the at least one landmark. The wearable device is further configured to determine a first current location based on the location information, and configured to use the wearable-end wireless module to broadcast the first current location and the user information to the at least one landmark, wherein the at least one landmark sends the first current location and the user information to the server. The monitoring device is configured to use the user information as reference to obtain the first current location from the server via the at least one landmark by the monitor-end wireless module.

The invention further provides a method for medical monitoring comprising the following steps: reading, by a monitoring device, a user information from a user tag of a wearable device; receiving, by the wearable device, a location information broadcasted by a landmark; determining, by the wearable device, a current location according to the location information and RSSI of the location information; broadcasting, by the wearable device, the current location and the user information to the landmark; receiving, by a server, the current location and the user information from the landmark; sending, by the wearable device, a physiological parameter to the server; sending, by the monitoring device, the user information to the server; receiving, by the monitoring device, the physiological parameter and the current location from the server based on the user information sent to the server.

The invention also provides wearable device for medical monitoring. The wearable device may comprise a storage comprising a positioning application, a processor configured to operate the positioning application to determine a current location, a physiological sensor configured to sense a physiological parameter from a user wearing the wearable device, a user tag configured to be read by a tag reader of a monitoring device, a wearable-end wireless module configured to send the current location and the physiological parameter to a server, wherein the user tag comprises a user information, wherein the monitoring device is configured to use the user information read from the user tag as reference to obtain the current location and the physiological parameter from the server using the user information read from the user tag as reference.

In view of the above, the invention provides a system for monitoring location and physiological parameters under a medical environment.

It should be understood, however, that this summary may not contain all aspects and embodiments of the present invention, that this summary is not meant to be limiting or restrictive in any manner, and that the invention as disclosed herein will be understood by one of ordinary skill in the art to encompass obvious improvements and modifications thereto.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment, and wherein.

In accordance with common practice, the various described features are not drawn to scale and are drawn to emphasize features relevant to the present disclosure. Like reference characters denote like elements throughout the figures and text.

DETAILED DESCRIPTION OF THE INVENTION

The present invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

It will be understood that the term "and/or" includes any and all combinations of one or more of the associated listed items. It will also be understood that, although the terms first, second, third etc. may be used herein to describe various elements, components, regions, parts and/or sections, these elements, components, regions, parts and/or sections should not be limited by these terms. These terms are only used to distinguish one element, component, region, part or section from another element, component, region, layer or section. Thus, a first element, component, region, part or section discussed below could be termed a second element, component, region, layer or section without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The description will be made as to the embodiments of the present invention in conjunction with the accompanying drawings in FIGS. 1 to 7. Reference will be made to the drawing figures to describe the present invention in detail, wherein depicted elements are not necessarily shown to scale and wherein like or similar elements are designated by same or similar reference numeral through the several views and same or similar terminology.

Figure 1:
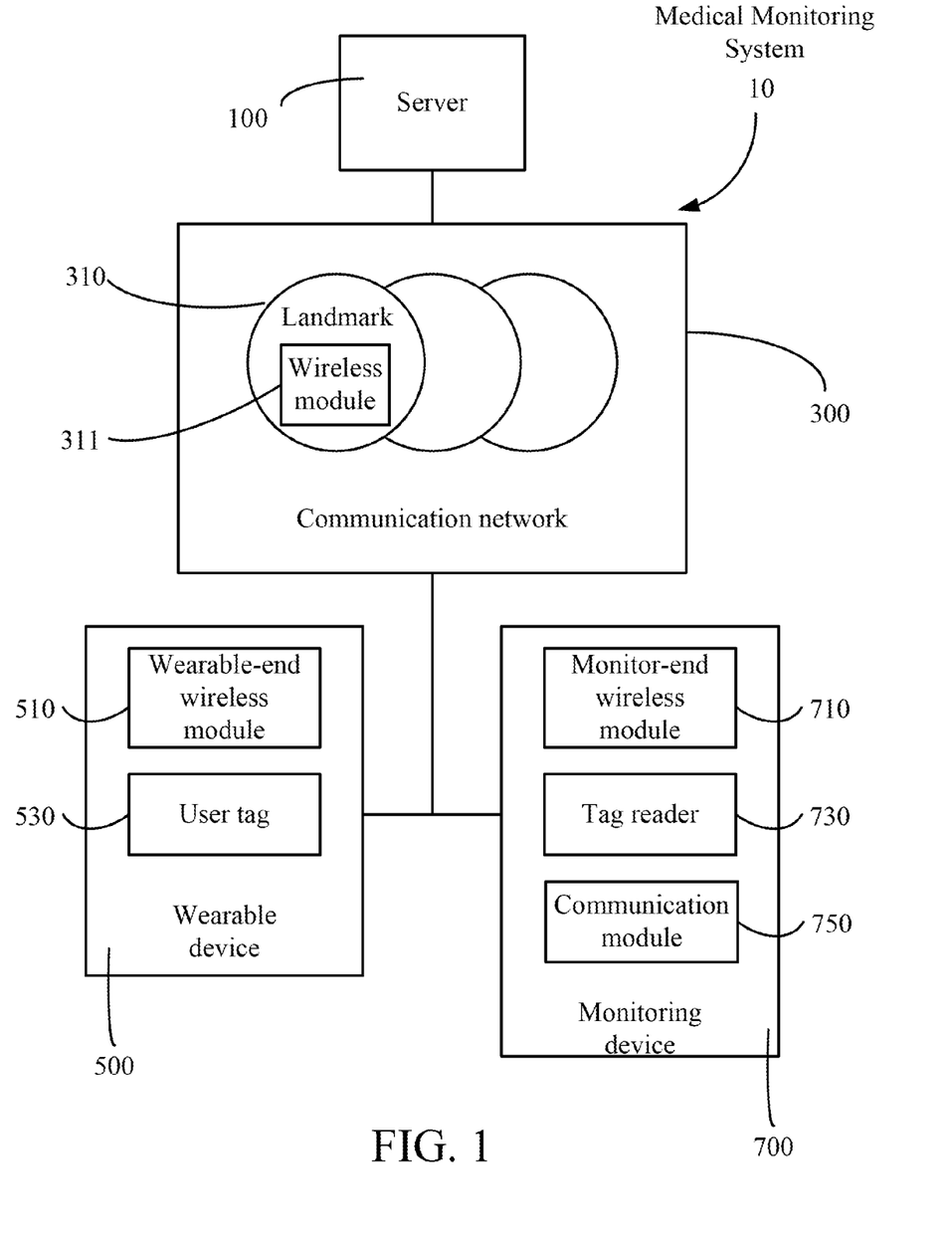
FIG. 1 is a schematic illustration of the medical monitoring system according to one embodiment of the present invention.

FIG. 1 schematically shows a medical monitoring system 10 according to one embodiment of the present invention.

The medical monitoring system 10 may comprise a server 100, a communication network 300, a wearable device 500, and a monitoring device 700. The communication network 300 may comprise at least one landmark 310, wherein each of the at least one landmark 310 may be assigned with a location information of its own. The server 100 may be connected to the at least one landmark 310. The at least one landmark 310 may comprise a wireless module 311, and be configured to broadcast the location information to any device with wireless capabilities within its range. The wireless module 311 may use Bluetooth, Wi-Fi, or any other ways for wireless communication. The wearable device 500 may comprise a wearable-end wireless module 510 and a user tag 530, wherein the wearable device 500 may be configured to use the wearable-end wireless module 510 to receive the location information from the at least one landmark 310. And the wearable device 500 may determine a current location according to the location information and a RSSI (received signal strength indicator). The wearable-end wireless module 510 may use Bluetooth, Wi-Fi, or any other ways for wireless communication. The user tag 530 may comprise user information of the user of the wearable device 500. The monitoring device 700 may comprise a monitor-end wireless module 710 and a tag reader 730, wherein the monitoring device 700 may use the tag reader 730 to read the user tag 530 to obtain the user information from the wearable device 500. The monitor-end wireless module 710 may use Bluetooth, Wi-Fi, or any other ways for wireless communication. The wearable device 500 may be configured to use the wearable-end wireless module 510 to broadcast the current location and the user information to the at least one landmark 310, and the at least one landmark 310 may send the current location and the user information to the server 100. The monitoring device 700 may use the monitor-end wireless module 710 to obtain the current location of the wearable device 500 from the server 100 directly or indirectly by referencing the user information read from the user tag 530. For example, the monitoring device 700 may obtain the current location from the server 100 via the at least one landmark 310, or the monitoring device 700 may obtain the current location from the server 100 by using a communication module 750, so that the monitoring device 700 is able to communicate with the server 100 without going through the at least one landmark 310. The communication module 750 may use Bluetooth, Wi-Fi, or any other ways for wireless communication.

In one embodiment of the present invention, the user tag 530 may be a RFID tag, a NFC tag, or any similar radio frequency based tag.

In one embodiment of the present invention, the at least one landmark 310 may connect to the server 100 wirelessly by Wi-Fi, Bluetooth, Zigbee, etc. Alternatively, the landmark 310 may connect to the server 100 with wire connection, such as PLC (power line communication), Ethernet, etc.

In one embodiment of the present invention, when there's a plurality of landmarks 310, the plurality of landmarks 310 may connect to one another wirelessly by Wi-Fi, Bluetooth, Zigbee, etc. Alternatively, the plurality of landmarks 310 may connect to one another with wire connection, such as PLC (power line communication), Ethernet, etc. It should be noticed that the network between the plurality of landmarks 310 may be in any type such as meshed network, star network, etc.

In one embodiment of the present invention, the landmark 310 may be an illumination device, or any other electrical appliance that may be connected to the grid or AC power source.

In one embodiment of the present invention, the user information may comprise personal information of the user of the wearable device 500, such as name, ID number, picture of the user, biometric information, physiological parameters, etc.

In one embodiment of the present invention, the location information may comprise coordinate, such as longitude, latitude, altitude, cylindrical coordinate or any other forms of three dimensional coordinate systems, wherein the coordinate may be a definite coordinate which is applicable in real world or a relative coordinate that is only applicable in a specific area where the at least one landmark 310 may be installed.

In one embodiment of the invention, the monitoring system 10 further comprises a sensing device (not shown) with a directional antenna, and the sensing device may be disposed in a specific space. When the wearable device 500 enters the specific space, the sensing device may detect the wearable-end wireless module 510 of the wearable device 500, and activates a gate control mechanism of the specific space to provide entry. The same approach applies to the monitoring device 700, wherein the sensing device may detect the monitor-end wireless module 710 instead to activate the gate control mechanism.

In one embodiment of the present invention, the monitoring system 10 further comprises a mobile nursing trolley (not shown) disposed with a host, and the host includes a sensing module. When the sensing module does not detect the monitoring device 700 within a sensing range, an input unit of the host enters a lock mode.

Figure 2:
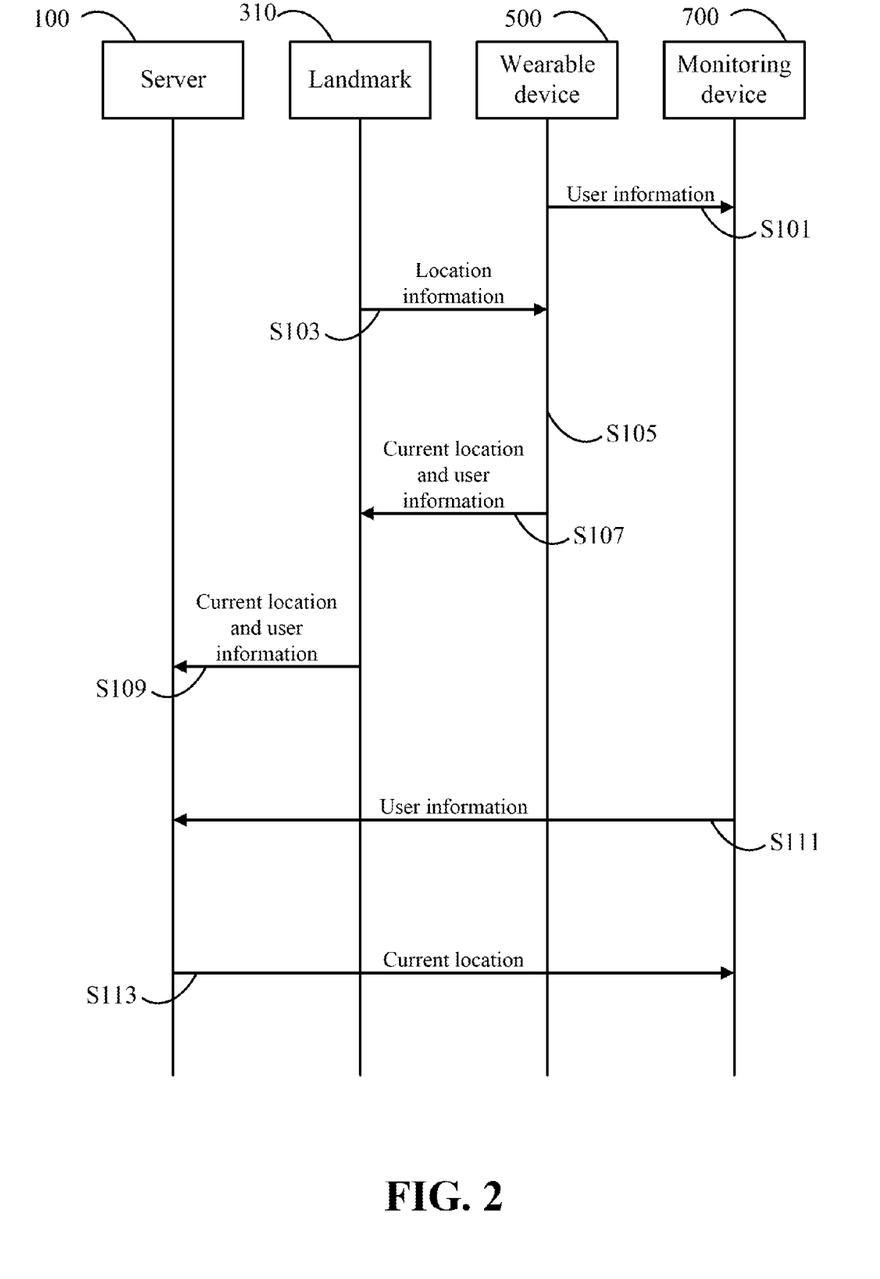
FIG. 2 is a schematic illustration of a method to use the medical monitoring system to obtain a current location of a wearable device according to one embodiment of the present invention.

FIG. 2 schematically shows a method to use the medical monitoring system 10 to obtain a current location of a wearable device 500.

Referring to FIG. 2, according to one embodiment of the present invention, the method to use the medical monitoring system 10 to obtain a current location of a wearable device 500 comprises the following steps:

S101: A monitoring device 700 may use the tag reader 730 to obtain a user information from a user tag 530 of the wearable device 500;

S103: At least one landmark 310 may use the wireless module 311 to broadcast at least one location information to the wearable device 500;

S105: The wearable device 500 determines a current location of the wearable device 500 according to the at least one location information and the RSSI;

S107: The wearable device 500 may use the wearable-end wireless module 510 to broadcast the current location and the user information to the at least one landmark 310;

S109: The at least one landmark 310 may send the current location and the user information to a server 100;

S111: The monitoring device 700 may use the communication module 750 to request for the current location of the wearable device 500 from the server 100 by sending the user information obtained from the wearable device 500 to the server 100;

S113: The monitoring device 700 may use the communication module 750 to obtain the current location of the wearable device 500 from the server 100 by using the user information sent as reference.

In one embodiment of the present invention, the step S101 may be carried out any time in between step S103 to S111 without affecting the result of the method.

In one embodiment of the present invention, in step S109, the landmark 310 may communicate with the server 100 with wired connection such as PLC, Ethernet, etc, or with wireless connection such as Wi-Fi, Bluetooth, etc.

In one embodiment of the present invention, in step S111 and/or S113, the monitoring device 700 may use the monitor-end wireless module 710 to communicate with the server 100 via the at least one landmark 310, wherein the communication between the at least one landmark 310 and the server 100 may be wired communication such as PLC, Ethernet, etc, or wireless communication such as Wi-Fi, Bluetooth, etc.

In one embodiment of the present invention, the user information may comprise personal information of the user of the wearable device 500, such as name, ID number, picture of the user, biometric information, physiological parameters, etc.

In view of the above, the medical monitoring system 10 may allow monitoring of the location of a user wearing the wearable device 500, and thus the user of the monitoring device 700 may be able to locate the user of the wearable device 500. In one embodiment of the present invention, the user wearing the wearable device 500 may be a patient or anyone needed to be monitored for medical purposes, and the user of the monitoring device 700 may be any healthcare provider such as doctor, nurse, etc.

In one embodiment of the present invention, the medical monitoring system 10 may further comprise an item that may be a mobile medical equipment, such as any one of a wheelchair, a sickbed, a nursing trolley, a mobile analgesic drugs hypodermic injection system device, a mobile radiation inspection device, a mobile cardiopulmonary blood pressure monitor, a mobile X-ray machine, a mobile ultrasound equipment and a mobile ultraviolet light irradiation lamp. A Bluetooth module as an item-end wireless module (not shown) may be configured in the mobile medical equipment. The Bluetooth module configured in the mobile medical equipment performs the step S103~105 to determine its current location like the wearable device 500, and then performs step S107~S109 to transmit its current location and a mobile medical equipment number instead of the user information to the server 100 via the communication network 300. Thus, the server 100 may keep track of the mobile medical equipment, and the monitoring device 700 may be able to obtain the current location of the mobile medical equipment by referencing the mobile medical equipment number. Furthermore, the mobile medical equipment may further comprise an accelerometer, wherein the accelerometer detects the motion of the mobile medical equipment. The accelerometer may be coupled to the item-end wireless module, so as to activate the item-end wireless module for tracking once the accelerometer detects any motion of the mobile medical equipment.

Figure 3:
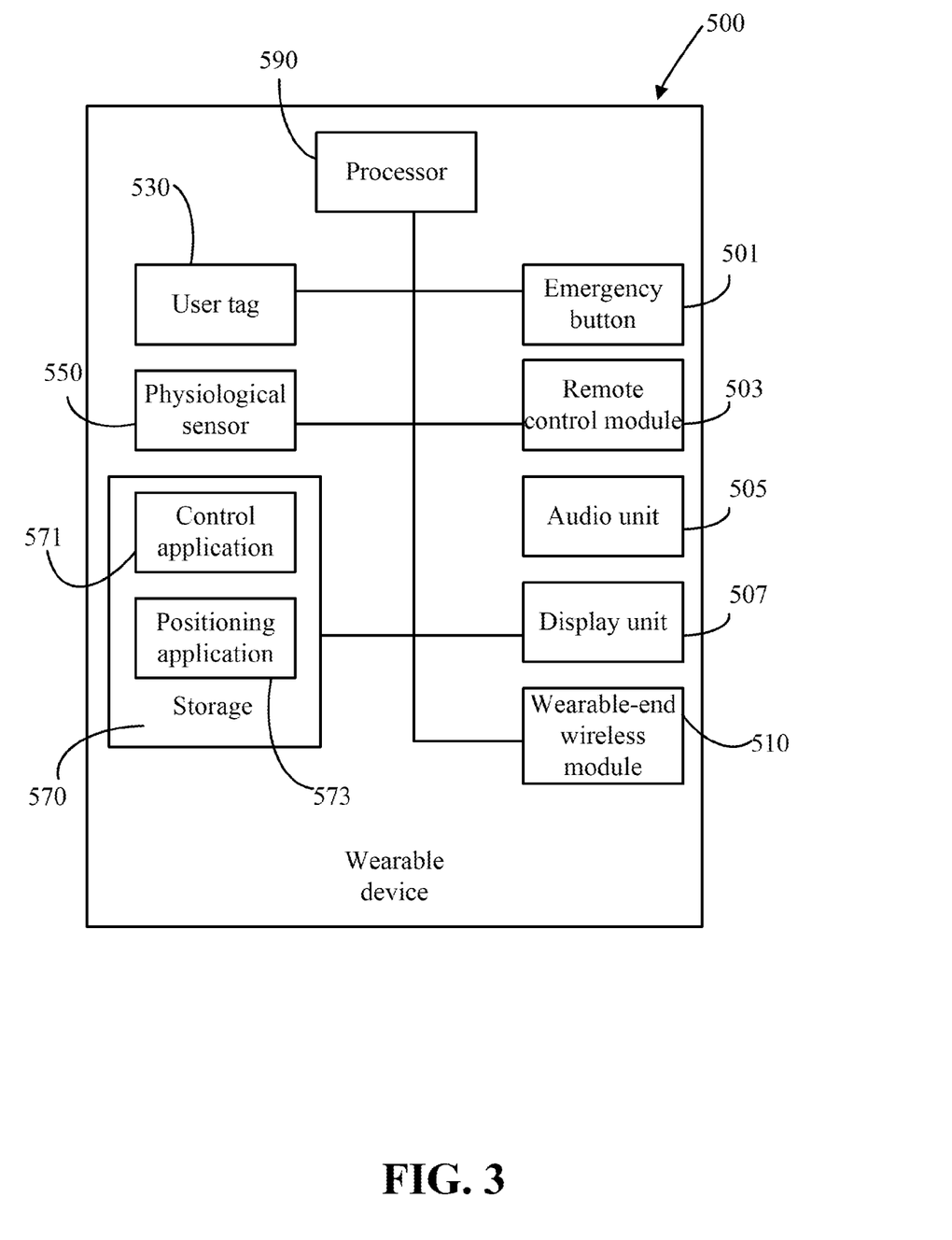
FIG. 3 is a schematic illustration of a wearable device of the medical monitoring system according to one embodiment of the present invention.

FIG. 3 schematically shows a wearable device 500 of the medical monitoring system 10 according to one embodiment of the present invention. The wearable device 500 may comprise a wearable-end wireless module 510, a user tag 530, a physiological sensor 550, a processor 590, an emergency button 501, a remote control module 503, an audio unit 505, a display unit 507, and a storage 570 which may be coupled to one another, wherein the storage 570 may comprise a control application 571 and a positioning application 573. The processor 590 may operate the control application 571 and the positioning application 573. The user tag 530 may comprise user information. Specifically, the user tag 530 may be RFID, NFC or any similar radio frequency based tag.

Referring to FIG. 3, according to one embodiment of the present invention, the wearable device 500 may use the wearable-end wireless module 510 to receive location information from a landmark 310, and utilize the positioning application 573 to determine a current location of the wearable device 500. Then, the wearable-end wireless module 510 may broadcast the current location together with the user information to the landmark 310, and the landmark 310 may send the current location and the user information to a server 100. Thus, the current location of the wearable device 500 may be tracked by the server 100. Furthermore, a monitoring device 700 may obtain the current location of the wearable device 500 by using the user information read from the user tag 530 as reference.

In one embodiment of the present invention, the physiological sensor 550 may sense physiological parameters of the user of the wearable device 500. For example, the physiological sensor may sense the physiological parameters of a patient wearing the wearable device 500. The physiological parameters may be sent to the server 100 via the landmark 310 for monitoring purpose, wherein the server may send the physiological parameters to the monitoring device 700 when the user information of the wearable device 500 may be provided as reference. Thus, a user of the monitoring device 700 may be able to monitor the health condition of the user of the wearable device 500 remotely. Alternatively, the physiological parameters may be stored in the user tag 530, and the user of the monitoring device 700 may read the user tag 530 for the physiological parameters if needed. For example, the user of the monitoring device 700 may be a healthcare provider doing a ward round. In addition, the physiological parameters may also be displayed by the display unit 507, so the user of the wearable device 500 may know his/her own health condition.

In one embodiment of the present invention, the physiological parameter may be temperature, pulse, respiratory rate, blood pressure, blood glucose, blood oxygen, etc.

In one embodiment of the present invention, the emergency button 501 may utilize the processor 590 to operate the control application 571 to send a distress signal, the last sensed physiological parameter, and the last determined current location to the sever 100. Then, the server 100 may pass the distress signal to the monitoring device 700. Alternatively, the distress signal, the last sensed physiological parameter, and the last determined current location may be sent to the monitoring device 700 directly if the monitoring device 700 is within the broadcasting range of the wearable-end wireless module 510. When the emergency button 501 is pressed, the wearable device 500 may also alarm the surrounding by utilizing the control application 571 to control the audio unit 505. For example, a patient with the wearable device 500 may press the emergency button 501 while feeling unwell or even life threatening such as not able to breathe.

In another embodiment of the present invention, the wearable device 500 may be configured to send the distress signal to the server 100 and/or the monitoring device 700 automatically when the physiological parameters are determined as critical. The wearable device 500 may determine whether the at least one physiological parameters is critical by using the control application 571 that may be preconfigured with a set of critical physiological parameter thresholds. Furthermore, the wearable device 500 may even alarm the surrounding with the audio unit 505 once the at least one physiological parameters is determined as critical.

In one embodiment of the present invention, when the distress signal may be sent to the monitoring device 700, the current location of the wearable device 500 may be sent from the server 100 to the monitoring device 700 via the landmark 310 by using the wearable-end wireless module 510 so that the user of the monitoring device 700 is able to reach the user of the wearable device 500. For example, a healthcare provider with the monitoring device 700 may be able to provide medical assistance to the patient with the wearable device 500 when the healthcare provider reach the patient by using the current location provided in the above approach.

In one embodiment of the present invention, the remote control module 503 may utilize the control application 571 to send a control signal via the wearable-end wireless module to control local infrastructure around the user of the wearable device 500, wherein the local infrastructure may be a landmark 310 with a wireless module 311 or any other electrical appliance with wireless capabilities that may be connected to the network 300. The local infrastructure may be a room light, an electrical bed, or an electrical curtain, etc. The remote control module 503 may be designed as a button or a set of buttons to control the local infrastructure. For example, a patient with the wearable device 500 may control the illumination of the room light, the incline of the electrical bed, or the opening of the electrical curtain, etc.

The wearable device 500 may also be realized by a smart phone so as to use the smart phone to serve as a facilitating tool for seeing the doctor to execute a clinic application (not shown). In addition, the clinic application may also be used to obtain information services provided by the hospital. Accordingly, it helps the nurse in calling the patients for seeing the doctor. Further, by using the medical monitoring system 10, the user may know of where treatment rooms are, as well as which one of the treatment rooms has fewer waiting patients. While waiting, the user may also obtain health education knowledge provided by the server 100 to further understand his/her illness as well as the related medical knowledge. Similarly, the user may know of his/her waiting order if there are many waiting patients. In addition, by using aforesaid method, the user does not have to wait outside the consulting room for long time; instead, the user may go to other places in the hospital (e.g., consumer site, post office, bank or health education places) after activating the clinic application.

Traditionally, when it comes to arrange the appointments for the patients, because a treatment period taken by the patients cannot be easily controlled, the patients usually need to wait outside the consulting room for long time. Accordingly, if a waiting time for the patient and accompany personnel can be reduced, in addition to substantially reduce a psychological burden and improve a time management for the patient, crowds inside the hospital may also be substantially reduced.

A waiting number for the appointment and a current called number may be informed by utilizing the clinic application of the smart phone or the wearable monitoring device 530. Accordingly, the user only needs to arrive at a couple minutes (e.g., 3 minutes) before appointment time. For the patients registered on-site or have the waiting number overdue, they may break in the waiting line according to their registration order. For the patients returned on-site for a result after the examination, they may join the waiting line together with the patients registered on-site and the patients having the waiting number overdue, but with a higher priority in the waiting line. No matter what, a number of the patients registered on-site may be maintained in a constant number (e.g., no more than 2 persons). Once the number of the patients registered on-site is less than 2, the nurse may then immediately notify the user to come through the notification method depicted in FIG. 6.

Figure 4:
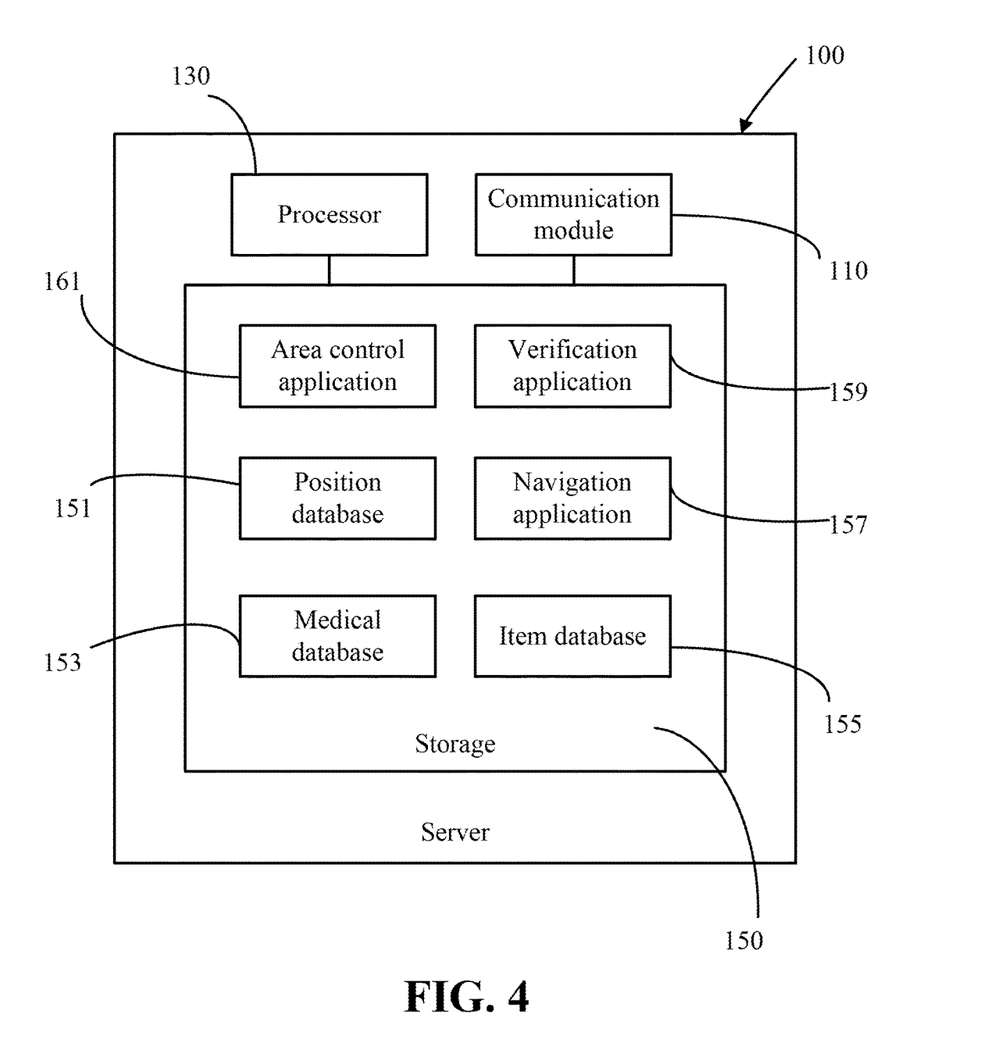
FIG. 4 is a schematic illustration of a server of the medical monitoring system according to one embodiment of the present invention.

FIG. 4 schematically shows a server 100 of the medical monitoring system 10 according to one embodiment of the present invention. The server 100 may comprise a communication module 110, a processor 130, and a storage 150 connected to the above. The storage 150 may comprise a position database 151, a medical database 153, an item database 155, a navigation application 157, a verification application 159, and an area control application 161. The position database may comprise location information such as the current location determined by a wearable device 500, item location, location of rooms, or a map of the area where at least one landmark 310 is installed. The medical database 153 may comprise user information, wherein the user information may comprise patient information, healthcare provider information, or medical information related to the patient information, such as prescription from doctor, surgical operation information, medical histories, etc. In addition, the medical database 153 may further comprise the physiological parameters. Furthermore, the medical database 153 may further comprise health knowledge for the wearable device 500 to access and read from the server 100. The item database may comprise medical item information such as drug information, medical equipment information, etc. It should be noticed that the medical database 153 and the item database 155 may be correlated with the position database in order to provide location of the user of wearable device 500, location of drug and/or medical equipment, etc. The processor 130 may be configured to operate the navigation application 157, verification application 159, and the area control application 161. The communication module 110 may be used for the communication between the server 100, a wearable device 500 and at least one landmark 310. Also, the communication module 110 may be used for the communication between the server 100 and the monitoring device 700, wherein the communication between may be through at least one landmark 310. It should be noticed that said communication may be wired communication or wireless communication.

In one embodiment of the present invention, the server 100 may receive a current location from a wearable device 500 via at least one landmark 310, wherein the current location may be saved in the position database 151. The current location may be marked on the map that may be sent by the communication module 110 to a monitoring device 700 for monitoring purposes. For example, a healthcare provider with the monitoring device 700 may request the current location of a patient wearing the wearable device 500 from the server 100 when the healthcare provider finds no one in the room while doing a ward round. The server 100 may correlate the user information of the patient in medical database 153 to the position database 151 to provide the map marked with the current location of the patient to the healthcare provider, and thus the healthcare provider may locate the patient according to the map.

In another embodiment of the present invention, the monitoring device 700 may determine a second current location, and send the second current location to the server 100. The position database 151 of the server 100 may save the second current location from the monitoring device 700, and the current location from the wearable device 500, so navigation may be provided to the user of the monitoring device 700 by using the navigation application 157. The navigation application 157 may correlate the map, current location, and the second current location, and thus determine a navigation route from the second current location to the current location on the map to provide navigation to the monitoring device 700. It should be noticed that the navigation may be provided automatically when emergency event takes place. For example, when a patient with the wearable device 500 presses the emergency button 501, the map with navigation route may be immediately provided to the healthcare provider with the monitoring device 700.

In one embodiment of the present invention, the monitoring device 700 may use the tag reader 730 to read an item tag of a medical item, wherein the item tag may comprise item information of the medical item, and the item information may be saved in the item database 155. The item information may be verified against a user information of the user that is about to be medicated by using the verification application 159. The monitoring device 700 may use the tag reader 730 to read a user tag 530 to obtain user information, and send the user information to the medical database 153 of the server 100. For example: when a healthcare provider with the monitoring device 700 is about to medicate a patient wearing the wearable device 500, the healthcare provider may scan both of the user tag 530 and the item tag with the monitoring device 700 tag reader 750, and send the user information and item information to the server 100 for verification. The server 100 may operate the verification application 159 and send a verification result to the monitoring device 700, wherein the verification result may be "correct medication" or "wrong medication", and the medical item may be any type of drug or medical equipment.

In one embodiment of the present invention, the server 100 may use the area control application 161 and the communication module 110 to send an area control signal to control the local infrastructure. In addition, the area control signal may be transmitted from the server 100 to at least one landmark 310 or via at least one landmark 310 to any other device connected to the communication network 300. The local infrastructure may be a landmark 310 with a wireless module 311 and/or any other electrical appliance with wireless capabilities that may be connected to the communication network 300. Examples of local infrastructure may be an illumination devices, a gate, air conditioning, etc, which may be around the area where the at least one landmark 310 is installed. For example, a hospital with at least one landmark 310 that is installed as an illumination device. In addition of the wireless module 311, the landmark 310 further comprises an illumination unit. The server 100 may utilize the area control application 161 to control the illumination of the landmark 310, wherein the server 100 may control the brightness of the illumination unit according to time such as dimmer in day time and/or brighter at night time.

In one embodiment of the present invention, the server 100 may further comprise an emergency application (not shown) in the storage 150, wherein the emergency application may also be operated by the processor 130. The emergency application may determine whether a physiological parameter sent from a wearable device 500 is critical, and may use the communication module 110 to send a distress signal together with a current location from the wearable device 500 to a monitoring device 700 if the physiological parameter received is critical. For example, a patient with the wearable device 500 may have physiological parameter sensed such as blood pressure value, and the blood pressure value may be sent to the server 100, wherein the server 100 may determine the blood pressure value as critical and therefore send a distress signal together with the current location of the wearable device 500 to a monitoring device 700. So, a healthcare provider with the monitoring device 700 may reach the patient with the current location received.

In one embodiment of the present invention, the item database 155 of the server 100 may comprise drug information, wherein the drug information each includes at least one of a pharmacology classification effect, a drug description and a drug image.

In one embodiment of the present invention, the verification application 159 may also verify a user of the wearable device 500 and/or monitoring device 700 according to the user information in the medical database 153, so the server 100 may utilize the area control application 161 to control the user's access to the area and/or within the area where the at least one landmark 310 is installed.

In one embodiment of the present invention, family members of a user wearing the wearable device 500 may access the server 100 via the monitoring device 700 or internet, so the family members may obtain the user's current location.

Figure 5:
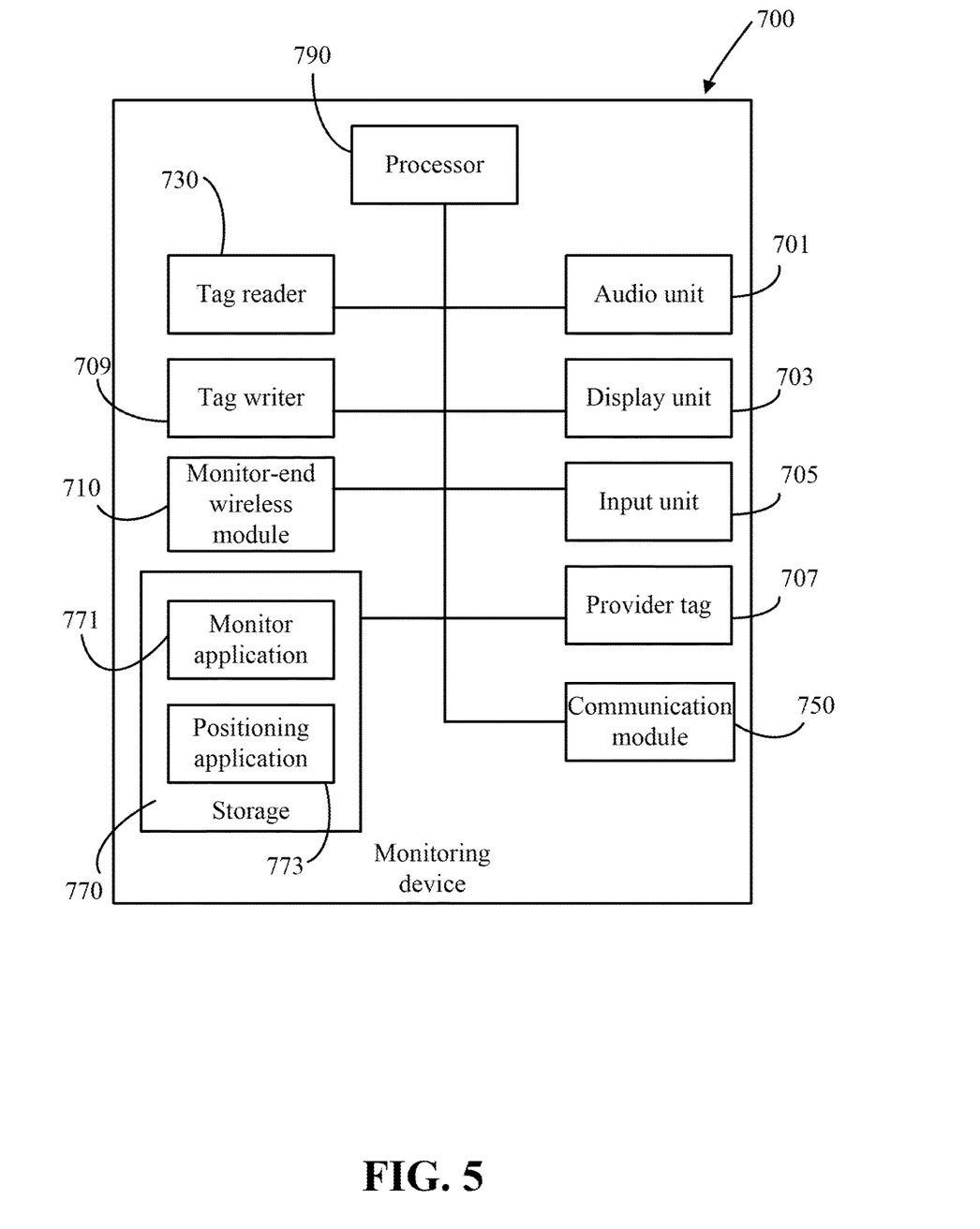
FIG. 5 is a schematic illustration of a monitoring device of the medical monitoring system according to one embodiment of the present invention.

FIG. 5 schematically shows a monitoring device 700 of the medical monitoring system 10 according to one embodiment of the present invention. The monitoring device 700 may comprise a monitor-end wireless module 710, a tag reader 730, a tag writer 709, a communication module 750, a processor 790, an audio unit 701, a display unit 703, an input unit 705, a provider tag 707, and a storage 770 coupled with one another, wherein the storage 770 may comprise a monitor application 771 and a positioning application 773. The monitoring device 700 may use the monitor-end wireless module 710 to communicate with a wearable device 500 and/or at least one landmark. The tag reader 730 may read a user tag 530 of the wearable device 50, and the tag writer 750 may write the user tag 530. The communication module 750 may be used for communication between the monitoring device 700 and a server 100, wherein the communication may be wired or wireless communication. The processor 790 may operate the monitor application 771 and the positioning application 773 in the storage 770. The audio unit 701 may output audio such as alarm, notification, reminder, etc. The display unit 703 may display text such as user information, or image such as portrait of the user, or map from a position database 151 in the server 100. The input unit 705 may be used to input information for the tag writer 709 or for editing information such as prescription, medical history, etc, in medical database 153 of the server 100, wherein the information input by the input unit 705 may be sent by the communication module 750 to the server 100. The provider tag may comprise healthcare provider information of the monitoring device 700 such as name of a doctor, a nurse, etc.

In one embodiment of the present invention, the provider tag 707 may be a RFID tag, a NFC tag, or any similar radio frequency based tag.

In one embodiment of the present invention, the monitoring device 700 may read and/or write the user tag 530 of the wearable device 500 by using the tag reader 730 and the tag writer 709. For example, a healthcare provider with the monitoring device 700 may use the tag reader 730 to read the user tag 530 of the wearable device 500 wore by a patient. Then, the monitoring device 700 may utilize the monitor application 771 to display the user information on the display unit 703, so the healthcare provider may see the patient's information. Furthermore, the healthcare provider may use the tag writer 709 and the input unit 705 to edit the user information if any update should be made. Furthermore, the healthcare provider information in the provider tag 707 may be attached together with the update, so the healthcare provider would be responsible for the updated user information. In addition, the monitoring device 700 may use the communication module 750 to send the updated user information to the medical database 153 of the server, so both user information in the wearable device 500 and the medical database 153 are synchronized.

In one embodiment of the present invention, the monitoring device 700 may use the monitor-end wireless module 710 to send a notification to the wearable device 500. For example, a healthcare provider with the monitoring device 700 may notify a patient to the clinical office, or remind the patient to take medication by inputting a notification with the input unit 705 and using the monitor-end wireless module 710 to send the notification to the patient wearing wearable device 500, wherein operation of monitoring application 771 may play the notification as voice by the audio unit 505 of the wearable device 500 or simply display the notification as image and/or text by the display unit 507 of the wearable device 500. The monitoring device 700 may communicate with the wearable device 500 via at least one landmark 310 when the wearable device 500 is not in the communication range of the monitor-end wireless module 710 of the monitoring device 7000, otherwise the monitoring device 700 may communicate with the wearable device 500 directly when the wearable device 500 is within the communication range of the monitor-end wireless module 710 of the monitoring device 700.

In one embodiment of the present invention, the monitoring device 700 may monitor health condition of a user of the wearable device 500 by receiving the physiological parameter from the server 100, wherein the physiological parameter may be sensed from a physiological sensor 550 of the wearable device 500 and the wearable device 500 may send the sensed physiological parameter to the server 100. Alternatively, the sense physiological parameter may be stored in a user tag 530 of the wearable device 500, and the monitoring device 700 may use the tag reader 730 to read the user tag 530 to obtain the physiological parameter. For example, a healthcare provider with the monitoring device 700 may read a patient's user tag 530 of the wearable device 500, wherein not only the user information of the patient but also the physiological parameter is read by the tag reader 730. Thus, the wearable device 700 may display both the user information and the physiological parameter on the display unit 703 by operating the monitor application 771.

In one embodiment of the present invention, the monitoring device 700 may use the monitor-end wireless module 710 to receive broadcasted location information from at least one landmark 310. The monitoring device 700 may use the positioning application 773 to determine a second current location based on the location information and the RSSI of the broadcasting from the at least one landmark 310. The monitoring device 700 may use the monitor-end wireless module 710 to send the second current location to a server 100 via the at least one landmark 310, and thus the second current location may be stored in the position database 151. The server 100 may utilize the navigation application 157 to mark the second current location on a map together with a current location of a wearable device 500 so as to form a map with navigation route between the second current location and the current location. Thus, the server may send the map to the monitoring device 700. For example, a healthcare provider with the monitoring device 700 may need to locate a patient wearing the wearable device 500 when emergency event takes place, thus the monitoring device 700 may request for navigation from the server 100. Then, the server 100 may utilize the navigation application 157 to provide a map with the navigation route from the second current location to the current location, and the monitoring device 700 may receive the map by using either communication module 750 or monitor-end wireless module 710, wherein the monitoring device 700 may receive the map by using monitor-end wireless module 710 via at least one landmark 310. Therefore, the healthcare provider may be able to follow the navigation route on the map to reach the patient and deal with the emergency event, wherein the emergency event may be critical physiological parameter sensed by the wearable device 500. It should be noticed that the positioning application 773 may comprise trilateration, triangulation or any other known positioning method.

In one embodiment of the present invention, the user of the monitoring device 700 may utilize the monitor application 771 and the communication module 750 to access the medical database 153 of the server 100. For example, a healthcare provider with the monitoring device 700 may use the communication module 750 to access the medical database 153 in order to obtain the user information and medical information corresponding to the user information of a patient that the healthcare provider is responsible for.

In one embodiment of the present invention, an outpatient management application (not shown) may be executed in the monitoring device 700 (e.g., a tablet computer or a smart phone) used by the nurse. In the outpatient management application, it is preset with a principle for each patient in which an average clinic time is set to 5 minutes, a waiting time is set to 10 minutes, and an appointment time is set to a fixed time period. For example, the waiting time set to 10 minutes basically aims to achieve a target that the person made the appointment will not wait for more than 10 minutes. That is, for each patient, a total time for clinic in the hospital will not exceed 30 minutes at most. If somehow the patient fails to arrive at the appointment time, the patients registered on-site may break in a waiting line for clinic according to their registration orders. Such provision may have the patients made the appointment arranged in the front two hour, so that each of the examination items may be completed within the clinic time for each patient. Moreover, working overtime for examination departments may also be avoided. A method of the registration includes, for example, sliding a health insurance card across an additional card reader on the monitoring device 700.

Figure 6:
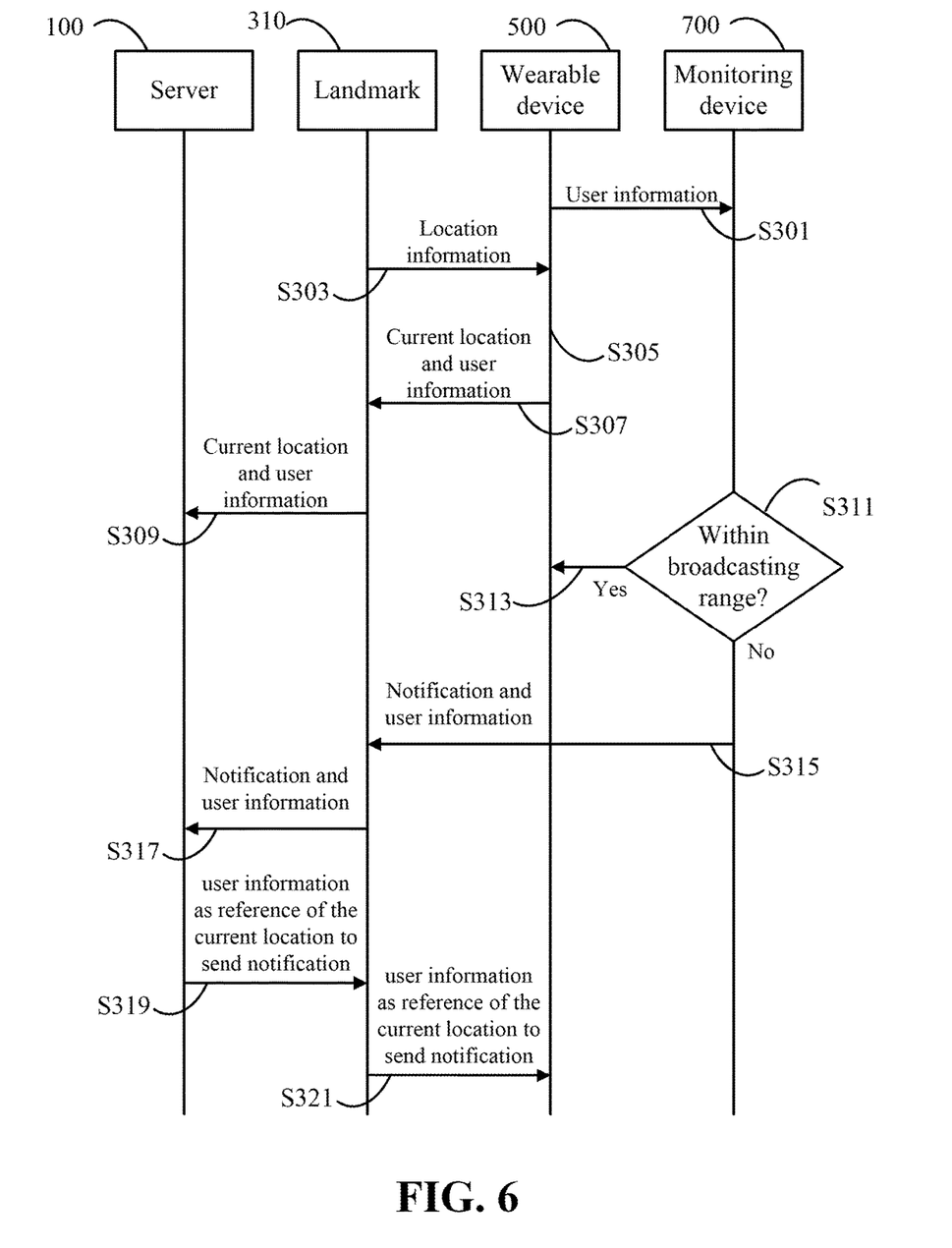
FIG. 6 is a schematic illustration of a method to use the medical monitoring system to send a notification from a monitoring device to a wearable device according to one embodiment of the present invention.

FIG. 6 schematically shows a method to use the medical monitoring system 10 to send a notification from a monitoring device 700 to a wearable device 500.

Referring to FIG. 6, according to one embodiment of the present invention, the method to use the medical monitoring system 10 to send a notification from a monitoring device 700 to a wearable device 500 comprises the following steps:

S301: A monitoring device 700 may use the tag reader 730 to obtain a user information from a user tag 530 of the wearable device 500;

S303: At least one landmark 310 may use the wireless module 311 to broadcast at least one location information to the wearable device 500;

S305: The wearable device 500 determines a current location of the wearable device 500 according to the at least one location information and the RSSI;

S307: The wearable device 500 may use the wearable-end wireless module 510 to broadcast the current location and the user information to the at least one landmark 310;

S309: The at least one landmark 310 may send the current location and the user information to a server 100;

S311: The monitoring device 700 may use the monitor-end wireless module 710 to scan the surrounding to determine whether the wearable device 500 is within the broadcasting range of the monitoring device 700;

S313: The monitoring device 700 determine the wearable device 500 is within the broadcasting range, and send a notification to the wearable device 500 by the monitor-end wireless module 710;

S315: The monitoring device 700 determine the wearable device 500 is not within the broadcasting range, thus sending a notification together with the user information to the at least one landmark 310 by the monitor-end wireless module 710;

S317: The at least one landmark 310 may send the notification and the user information to the server 100;

S319: The server 100 may use the user information as reference of the current location to send the notification to the at least one landmark 310;

S321: The at least one landmark 310 may use the wireless module 311 to send the notification to the wearable device 500 by using the user information as reference of the current location.

In one embodiment of the present invention, the step S301 may be carried out any time before the step S313.

In one embodiment of the present invention, the monitoring device 700 may send the notification to the wearable device 500 without step S311 and S313.

In one embodiment of the present invention, in step S309 and S317, the landmark 310 may communicate with the server 100 with wired connection such as PLC, Ethernet, etc, or with wireless connection such as Wi-Fi, Bluetooth, etc. It should be noticed that the same communication in opposite direction as in step S319 may apply the same.

In one embodiment of the present invention, the user information may comprise personal information of the user of the wearable device 500, such as name, ID number, picture of the user, biometric information, physiological parameter, etc.

In one embodiment of the present invention, the step S315 and S317 may be combined into one step that the monitoring device 700 may send the notification and the user information to the server 100 without passing the at least one landmark 310, wherein the notification and the user information may be sent to the server 100 directly by using the communication module 750.

In view of the above, the medical monitoring system 10 may allow the monitoring device 700 to send a notification to the wearable device 500 as long as the wearable device 500 is within the communication range of the at least one landmark 310.

Figure 7:
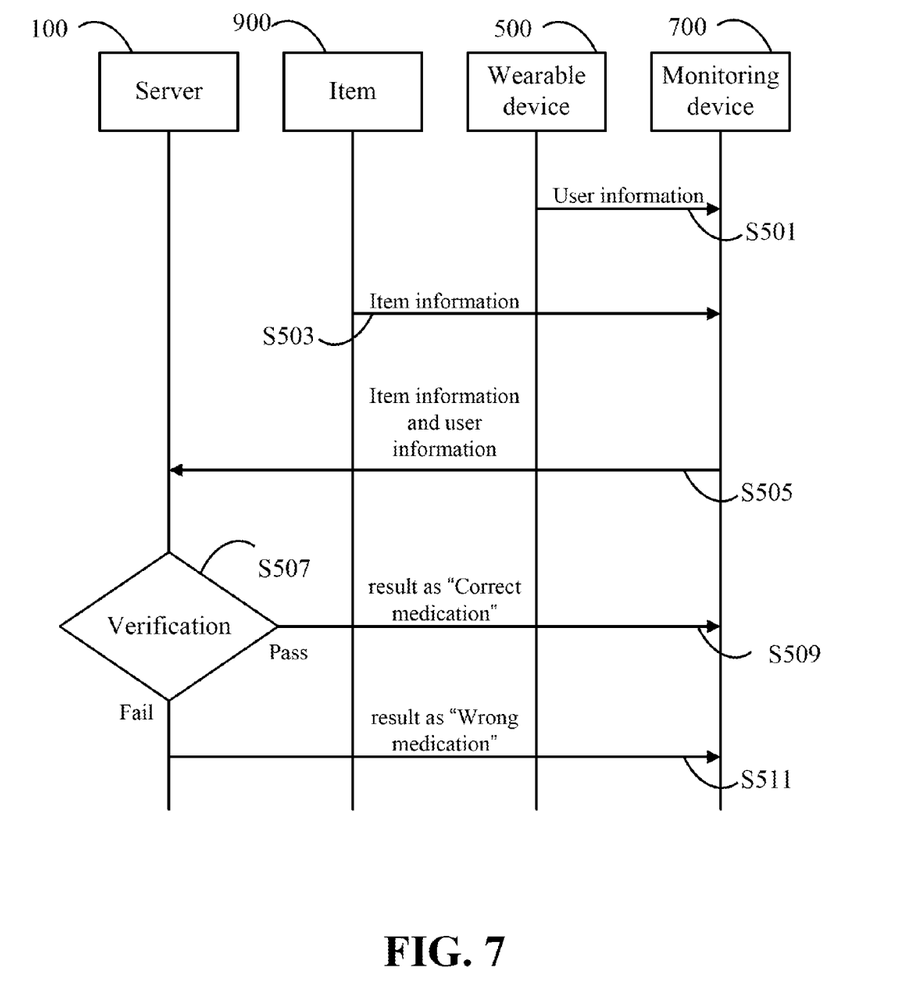
FIG. 7 is a schematic illustration of a method to use the medical monitoring system to verify an item against a patient wearing a wearable device according to one embodiment of the present invention.

FIG. 7 schematically shows a method to use the medical monitoring system 10 to verify an item 900 against a patient wearing a wearable device 500.

Referring to FIG. 7, according to one embodiment of the present invention, the method to use the medical monitoring system 10 to verify an item 900 against a patient wearing a wearable device 500 comprises the following steps:

S501: A monitoring device 700 of the medical monitoring system 10 may read a user tag 530 of the wearable device 500 by a tag reader 730 to obtain a user information of the patient;

S503: The monitoring device 700 may use the tag reader 730 to read an item tag of the item 900 to obtain an item information;

S505: The monitoring device 700 may send both the user information and the item information to a server 100 of the medical monitoring system 10;

S507: The server 100 may operate a verification application 159 to verify the item information against the user information by matching them;

S509: The server 100 may send a verification result as "Correct medication" to the monitoring device 700 if the item 900 pass the verification, so the item 900 may be provided to the patient;

S511: The server 100 may send a verification result as "Wrong medication" to the monitoring device 700 if the item 900 fails the verification, thus item 900 withdrawn.

In one embodiment of the present invention, the item 900 may be drug to be medicated to the patient, or medical equipment, and the user information may comprise transcription, medical history, surgical history, etc. For example, a healthcare provider with the monitoring device 700 may use the tag reader 730 to read the patient's user information that may be a transcription, and the item information that may be a drug information, and send these information to the server 100 that may match the drug to the transcription to make sure the patient is medicated correctly.

In one embodiment of the present invention, the monitoring device 700 may update the user tag 530 by using a tag writer 709 after the step S509. For example, a healthcare provider with the monitoring device 700 may update a patient's user information of the user tag 530 such as medical history after medication. Therefore, the medication done by the healthcare provider may be recorded for further use. In addition, the healthcare provider may also send the updated user information to the server 100 so the user information at the server 100 and patient's user tag 530 may be synchronized. Alternatively, the healthcare provider may use the input unit 705 with the monitor application 771 to manually edit the user information in a medical database 153 of the server 100.

In one embodiment of the present invention, the monitoring device 700 may request for the user information saved in the medical database 153 of the server 100 after step S511. For example, a healthcare provider with the monitoring device 700 may use the monitor application 771 to request the user information of a patient from the medical database 153 of the server 100 to double-check and understand why the medication provided fail the verification in step S507, and thus the healthcare provider may be able to provide correct medication to the patient with the help of medical history and item information of medication. In addition, the healthcare provider may use the tag writer 709 to update the patient's user tag 530 on the wearable device 500 by using the input unit 705. Furthermore, the healthcare provider may also manually update the user information of the patient on the medical database 153 as mentioned before or simply send the updated user information of the user tag 530 to the server 100.

In one embodiment of the present invention, the communication between the monitoring device 700 and the server 100 may be a direct communication or indirect communication. The indirect communication may be done by using the communication module 110 and monitor-end wireless module 710 to pass at least one landmark 310 in between, and the direct communication may be done by using communication module 110 and communication module 750 without any landmark 310.

In one embodiment of the present invention, the item tag may be replaced with 2D-bar code instead, so that the monitoring device 700 should comprise a 2D-bar code reader to obtain the item information.

Previous descriptions are only embodiments of the present invention and are not intended to limit the scope of the present invention. Many variations and modifications according to the claims and specification of the disclosure are still within the scope of the claimed invention. In addition, each of the embodiments and claims does not have to achieve all the advantages or characteristics disclosed. Moreover, the abstract and the title only serve to facilitate searching patent documents and are not intended in any way to limit the scope of the claimed invention.

What is claimed is:

1. A medical monitoring system, comprising:
   a plurality of landmark with a wireless module within each landmark are configured to broadcast a location information of each landmark; and
   a server connected to the plurality of landmarks; and
   a wearable device comprising a wearable-end wireless module and a physiological sensor for sensing a physiological parameter of a user of the wearable device; and
   a monitoring device comprising a monitor-end wireless module,
   wherein the wearable device is configured to use the wearable-end wireless module to receive first location information of a plurality of location information from the plurality of landmarks,
   wherein the wearable device is configured to determine a first current location of the wearable device based on first location information of a plurality of location information from the plurality of landmarks and a first received signal strength indicator, and the wearable device uses the wearable-end wireless module to broadcast the first current location of the wearable device and the physiological parameter to one landmark from the plurality of landmarks;
   wherein one landmark from the plurality of landmarks sends the first current location of the wearable device and the physiological parameter to the server; and
   wherein the monitoring device is configured to use the monitor-end wireless module to receive second location information of a plurality of location information from the plurality of landmarks, and the monitoring device is configured to determine a second current location of the monitoring device based on the second location information of a plurality of location information from the plurality of landmarks and a second received signal strength indicator, and the monitoring device uses the monitor-end wireless module to broadcast the second current location of the monitoring device to one landmark from the plurality of landmarks;
   wherein one landmark from the plurality of landmarks sends the second current location of the monitoring device to the server; and
   wherein the server is configured to send the first current location of the wearable device and the physiological parameter to the monitoring device according to the second current location of the monitoring device after the server determines the physiological parameter is critical.

2. The medical monitoring system according to claim 1, wherein the wearable device is configured to send a distress signal to the server via one landmark from the plurality of landmarks, and the server is configured to send the first current location of the wearable device with the distress signal to the monitoring device.

3. The medical monitoring system according to claim 1, wherein the wearable device further comprises an emergency button configured to be activated to send a distress signal to the server via one landmark from the plurality of landmarks.

4. The medical monitoring system according to claim 1, wherein a distress signal is sent to the server by the wearable device via the at least one landmark when the physiological parameters is determined as critical by the wearable device.

5. The medical monitoring system according to claim 1, wherein the monitoring device further comprises a display unit and the display unit is adapted to display a map with the first current location of the wearable device.

6. The medical monitoring system according to claim 1, wherein the server is configured to provide a navigation route between the first current location of the wearable device and the second current location of the monitoring device on a map to the monitoring device.

7. The medical monitoring system according to claim 6, wherein the monitoring device further comprises a display unit to display the map with the navigation route.

8. The medical monitoring system according to claim 1, wherein the monitoring device is configured to send a notification comprising notifying a user wearing the wearable device from a healthcare provider to the wearable device directly when the wearable device is within communication range of the monitor-end wireless module.

9. The medical monitoring system according to claim 1, wherein the monitoring device is configured to send a notification comprising notifying a user wearing the wearable device from a healthcare provider to the wearable device indirectly via one landmark from the plurality of landmarks and the server when the wearable device is not within communication range of the monitor-end wireless module.

10. The medical monitoring system according to claim 1, further comprising:
    a medical item with an item tag,
    wherein the monitoring device with a tag reader is configured to use the tag reader to read an item information from the item tag.

11. The medical monitoring system according to claim 10, wherein the wearable device comprises a user tag, the monitoring device with the tag reader is configured to use the tag reader to read a user information from the user tag, and the monitoring device is further configured to send the item information and the user information to the server for verification.

12. The medical monitoring system according to claim 11, wherein the server performs the verification by matching the item information to a prescription corresponding to the user information in the server.

13. The medical monitoring system according to claim 1, further comprising:
    an item with an item-end wireless module and an item information,
    wherein the item is configured to use the item-end wireless module to receive the location information of one landmark from the plurality of landmarks from the at least one landmark,
    wherein the item is configured to determine a third current location of the item based on the location information of one landmark from the plurality of landmarks, and use the item-end wireless module to broadcast the third current location of the item and the item information to one landmark from the plurality of landmarks;
    wherein one landmark from the plurality of landmarks sends the third current location of the item and the item information to the server.

14. The medical monitoring system according to claim 1, further comprising:
    a sensing device with a directional antenna,
    wherein the sensing device activates a gate control mechanism to provide entry when the sensing device utilize the directional antenna to sense the wearable device and/or the monitoring device.

15. The medical monitoring system according to claim 1, further comprising:
    a trolley with a host,
    wherein the host comprise a sensing module and an input unit, when the sensing module does not detect the monitoring device within a sensing range, the input unit of the host enters a lock mode.

16. A method for medical monitoring, comprising:
    a: reading, by a monitoring device, a user information from a user tag of a wearable device;
    b: receiving, by the wearable device, a location information of a landmark from the plurality of landmarks broadcasted by the landmark from the plurality of landmarks;
    c: determining, by the wearable device, a current location of the wearable device according to the location information of the landmark from the plurality of landmarks and RSSI of the location information;
    d: broadcasting, by the wearable device, the current location of the wearable device and the user information to the landmark from the plurality of landmarks;
    e: receiving, by a server, the current location of the wearable device and the user information from the landmark from the plurality of landmarks;
    f: sending, by the wearable device, a physiological parameter to the server;
    g: sending, by the monitoring device, the user information to the server;
    h: receiving, by the monitoring device, the physiological parameter and the current location of the wearable device from the server based on the user information sent to the server.

17. The method for medical monitoring according to claim 16, wherein step f further comprises sending a distress signal by the wearable device to the server, and step h further comprises receiving a distress signal by the monitoring device from the server.

18. The method for medical monitoring according to claim 16, wherein step h further comprises receiving a map with a navigation route by the monitoring device from the server.

19. A wearable device for medical monitoring, comprising:
    a storage comprising a positioning application; and
    a processor configured to operate the positioning application to determine a current location of the wearable device, wherein the processor determines the current location of the wearable device based on a location information of a landmark from the plurality of landmarks broadcasted from the landmark from the plurality of landmarks and RSSI of the broadcast; and
    a physiological sensor configured to sense a physiological parameter from a user wearing the wearable device; and
    a user tag configured to be read by a tag reader of a monitoring device; and
    a wearable-end wireless module configured to send the current location of the wearable device and the physiological parameter to a server;
    wherein the user tag comprises a user information, and wherein the monitoring device is configured to request the current location of the wearable device from the server by sending the user information to the server, and is further configured to obtain the first current location of the wearable device from the server by using the user information sent as reference.

20. The wearable device for medical monitoring according to claim 19, wherein the storage further comprises a control application that is configured to be operated by the processor to display the physiological parameter on a display unit.

21. The wearable device for medical monitoring according to claim 19, further comprising an emergency button, wherein the emergency button is configured to be activated by a user of the wearable device to send a distress signal to the monitoring device.

22. The wearable device for medical monitoring according to claim 19, wherein the storage further comprising a control application that may be operated by the processor to determine whether the physiological parameter is critical.

23. The wearable device for medical monitoring according to claim 19, further comprising a remote control module to control the illumination of the landmark, wherein the landmark is an illumination device.

24. The wearable device for medical monitoring according to claim 19, wherein the physiological parameter is adapted to be stored in the user tag and the monitoring device is configured to use the tag reader read the user tag to obtain the physiological parameter.

25. The medical monitoring system according to claim 1, wherein the monitoring device further comprises a tag writer and an input unit, the tag writer is configured to write the user tag, the input unit is configured to input information for the tag writer or to edit information of the server.

26. The medical monitoring system according to claim 1, wherein the wearable device comprises a user tag, the user tag comprises user information of the user of the wearable device, the wearable device is configured to broadcast the user information to one landmark from the plurality of landmarks, one landmark from the plurality of landmarks sends the user information to the server, the monitoring device is configured to request the first current location of the wearable device from the server by sending the user information to the server via the at least one landmark by the monitor-end wireless module, and is further configured to obtain the first current location of the wearable device from the server by using the user information sent as reference via the at least one landmark by the monitor-end wireless module.

27. The medical monitoring system according to claim 1, wherein the server comprises a medical database comprising user information, the monitoring device is configured to use the monitor-end wireless module to access the medical database of the server to obtain the user information.

* * * * *